United States Patent [19]

Cargill et al.

[11] Patent Number: 5,515,169
[45] Date of Patent: May 7, 1996

[54] SPECTRAL WAVELENGTH DISCRIMINATION SYSTEM AND METHOD FOR USING

[75] Inventors: Robert L. Cargill, San Jose; Erich Gombocz, Menlo Park; Claudio I. Zanelli, Sunnyvale; Basil Swaby, Santa Rosa, all of Calif.

[73] Assignees: Labintelligence Inc, Menlo Park; Optical Coating Laboratory, Inc., Santa Rosa, both of Calif.

[21] Appl. No.: 136,212

[22] Filed: Oct. 13, 1993

(Under 37 CFR 1.47)

[51] Int. Cl.⁶ .............................. G01N 21/64; G02B 5/28
[52] U.S. Cl. .......................... 356/417; 356/416; 356/344; 250/226; 359/589; 359/634
[58] Field of Search ..................................... 356/300, 402, 356/416, 417, 419, 425, 344; 250/226; 359/583, 589, 634

[56] References Cited

U.S. PATENT DOCUMENTS

| | | |
|---|---|---|
| 3,528,725 | 9/1970 | Barkley . |
| 3,926,508 | 12/1975 | Harmsen et al. . |
| 4,047,805 | 9/1977 | Sekimura . |
| 4,415,233 | 11/1983 | Itoh et al. . |
| 4,756,602 | 7/1988 | Southwell et al. . |
| 4,805,555 | 2/1989 | Itoh . |
| 4,957,371 | 9/1990 | Pellicori et al. .................. 356/419 |
| 5,104,512 | 4/1992 | Gombocz et al. . |

FOREIGN PATENT DOCUMENTS

55-142220 11/1980 Japan ....................................... 356/416

OTHER PUBLICATIONS

Dobrowolski, "Subtractive Method of Optical Thin–Film Interference Filter Design," *Applied Optics* (1973) 12: 1885–1893.

*Primary Examiner*—F. L. Evans
*Attorney, Agent, or Firm*—Bertram I. Rowland

[57] ABSTRACT

A spectral wavelength discrimination system and method for using are provided which allows the wavelength of a beam of radiation to be accurately determined using compact inexpensive optics and electronics. The system is particularly useful for identifying the emission wavelength of a multi-component marker system which includes a plurality of components having different wavelength ranges. The system comprises a wavelength selective beamsplitter, termed a Linear Wavelength Filter, that directs predetermined fractions of the beam at each wavelength into each of two output beams. The intensities of these output beams are measured. The measurements and selected system parameters, including the beamsplitter spectral characteristics and the detector sensitivity characteristics are used in a special algorithm for performing Fourier based wavelength-dispersive analysis. The unique solution of the Fourier based analysis is the wavelength of the beam of radiation. The system employs various optical components and structures to achieve the desired spatial resolution and sensitivity. Multiple channel devices and other special configurations are also described.

14 Claims, 6 Drawing Sheets

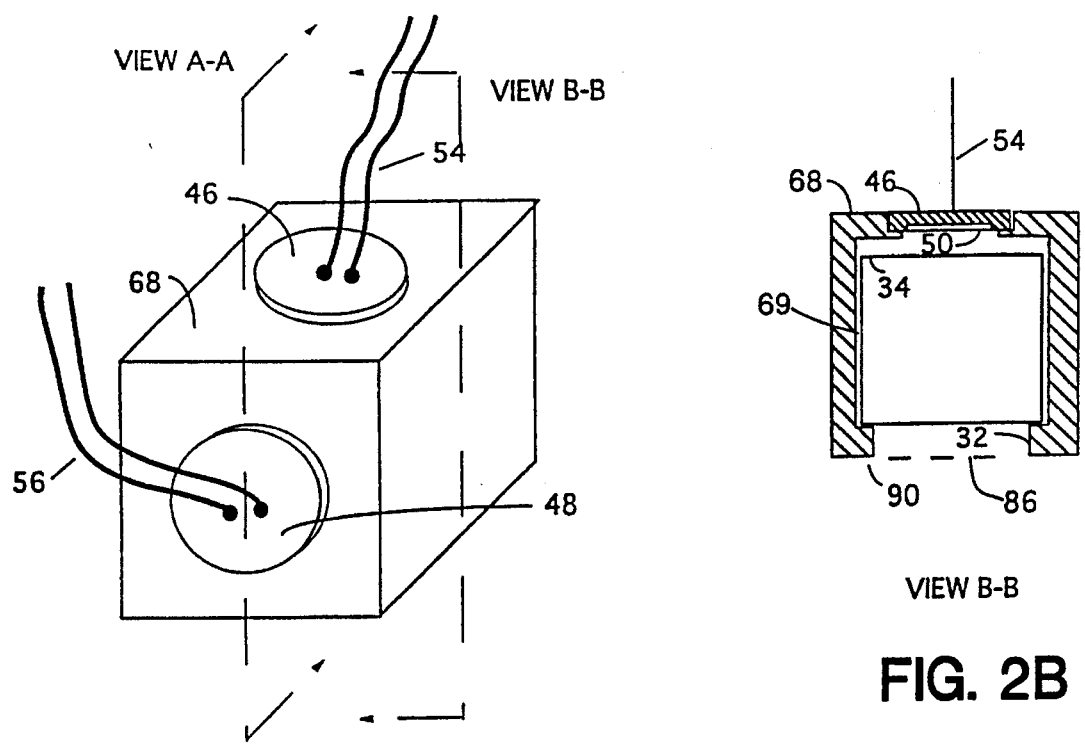
FIG. 2A
FIG. 2B
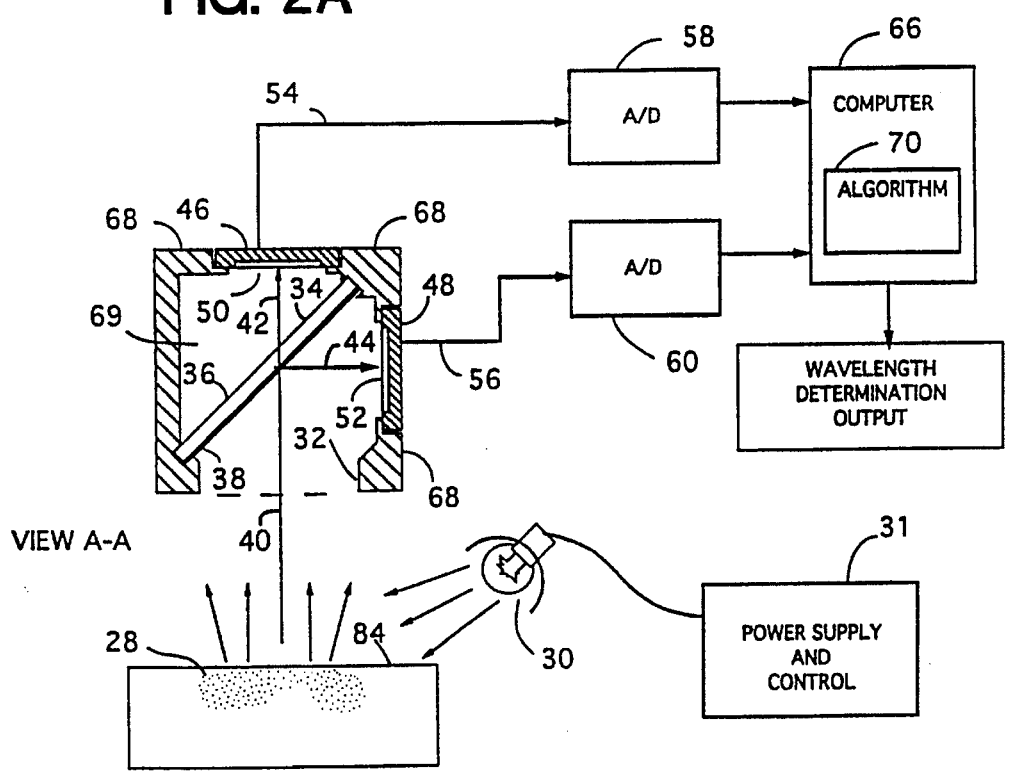
FIG. 2C

SPECTRAL WAVELENGTH DISCRIMINATION SYSTEM AND METHOD FOR USING

TECHNICAL FIELD

This invention relates to systems and methods for determining the wavelength of a beam of radiation.

BACKGROUND

Apparatus and methods for determining spectral wavelength characteristics of radiation are known in the art, but they generally require relatively complex and expensive optical systems, detectors, and electronics. The complexity of the prior art systems either diminishes reliability and results in greater measurement-to-measurement and system-to-system variability or require expensive equipment.

Reliance on conventional filters, prisms, gratings, optical modulators, and so forth, to filter or separate wavelengths from a beam, has constrained the design of conventional systems. Inexpensive and compact configurations that are stable, have multiple measurement channels, and have the required dynamic range and sensitivity, are not available.

While dichroic or interference filters and beamsplitters have been used as components of the spectral filtration scheme in some of these conventional systems, they have had three significant attributes that limited the reduction in system cost, increased the size, and limited overall system performance. First, while these filters are used to selectively transmit certain wavelengths of radiation and reflect other wavelengths, they were not used with the intention to transmit and reflect fractional amounts of the same wavelengths. Second, the transition region between the spectral regions of high transmission and high reflection is spectrally narrow, usually about 60 nm or less, and the transfer characteristic of the transition region is usually non-linear, and of only incidental importance to performance. Third, the transfer characteristic in the wavelength regions on either side of the transition region is of primary importance and is optimized for the transmission or reflection of all the wavelengths in the respective regions.

A typical prior-art dichroic beamsplitter characteristic and its complement with these attributes is illustrated in FIG. 1, which shows a reflective region 22, a transition region 24, and a transmissive region 26. The sharp transition between $\lambda_2$ and $\lambda_3$ is important for achieving the desired color separation in the dichroic beamsplitter. The flat transfer characteristic between $\lambda_1$ and $\lambda_2$ and between $\lambda_3$ and $\lambda_4$ assure that the beamsplitter separates the beam but does not introduce additional intensity variation as a function of wavelength.

There is a need in numerous fields for a simple, compact, inexpensive, mobile, reliable, multi-channel system and method for determining the wavelength of a beam of radiation with high sensitivity. For example, in the field of gel electrophoresis, a multi-component fluorescent marker system is used to differentially and uniquely label sample constituents along one or more gel electrophoresis channels. The presence and identity of sample constituents at locations along each channel are determined from the emission wavelength of the associated marker at each location. The magnitude of the emission may vary over a large range but the intensity is low because the amount of marker must be limited based on the small amount of sample present. Therefore, an apparatus would have significant application that has a dynamic range of about four orders of magnitude, and sufficient sensitivity to detect the emissions from smaller than ten nanogram amounts of fluorescer, and further capable of accurately determining the wavelengths and, thus, the sample constituents corresponding to those emissions. A comparable need exists in the field of enzyme analysis. In the field of scanning systems, there is a need for a system that can rapidly determine the color of regions of a document using a single scan of the document, a minimum number of detectors, and a fast simple color determination algorithm.

Relevant Literature

U.S. Pat. Nos. 4,957,371; 4,805,555; 4,756,602; 4,415,233; 4,047,805; 3,926,508; and 3,528,725 discuss the design and preparation of optical coatings. A description of a gel electrophoresis apparatus with a photometer for determining fluorescent wave length is found in U.S. Pat. No. 5,104,512.

Dobrowski, J. A., Applied Optics (1973)12:1885–1893 describes a method of design for a dielectric interference filter with a specified spectral performance.

SUMMARY OF THE INVENTION

An efficient radiation wavelength determination system and method are provided using inexpensive optics and electronics for determining the wavelength of a beam of radiation received from a sample. The system comprises an optical system to gather and direct received light; a Linear Wavelength Filter to separate radiation from a sample into two beams; a detector receiving each beam to sense the amount of radiation; and computation means including an algorithm for determining the wavelength of received light. The system may optionally comprise a radiation source to irradiate the sample.

A multi-channel system is also provided that provides multiple simultaneous wavelength determinations for radiation emitted by several samples. An ultra-compact sealed single-channel unit is provided for measurements in remote or unusual environments.

DESCRIPTION OF THE DRAWINGS

FIG. 2 is an illustration of an embodiment of the system according to the present invention, and wherein FIG. 2A is a perspective view of the exterior of the system housing, FIG. 2B is a sectional view through one plane, and FIG. 2C is a sectional view through a second plane and includes other operational system components.

DESCRIPTION OF THE SPECIFIC EMBODIMENTS

Figure 1:
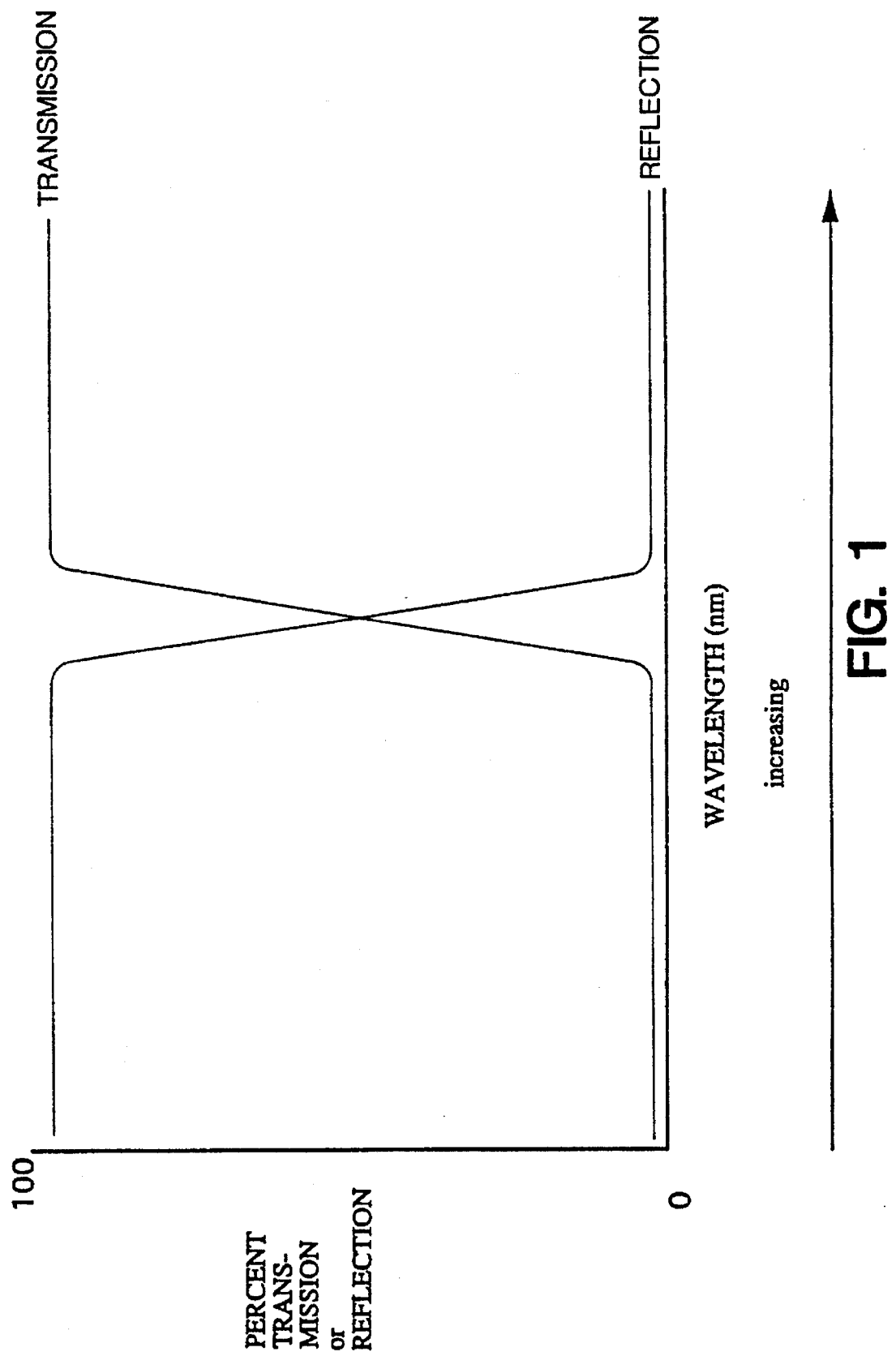
FIG. 1 is an illustration of a typical prior-art dichroic filter transmission-reflection versus wavelength characteristic.

A spectral wavelength discrimination system and method are provided which allows for the determination of the wavelength of radiation emitted by, transmitted through, or reflected from virtually any source or sample, particularly where the light source is relatively small and may be subject to substantial background. The emitted radiation is typically visible wavelength light, but may be any radiation in the range between from about 250 nm to 1100 nm, specifically from about 300 nm to 800 nm.

The system is useful in detection of monochromatic beams of light, i.e. a beam of light comprising a very narrow spectral band of wavelengths. The system finds particular application with gel electrophoresis and like systems, where it is necessary to determine light at different wavelength ranges during the same or different runs. For gel electrophoresis one is concerned with being able to detect small fluorescent bands, discriminating the light from the bands, as against background, where particularly plastic materials, such as the gel plate, can be highly fluorescent. By providing for wavelength discrimination over a broad wavelength range, runs may be multiplexed, where different components may be distinguished by the wavelength of the emitted light. Also, the device may be used with different fluorophores at different times, without changing the optical system.

The subject apparatus provides means for narrowing and focusing the light from a small area, such as a gel electrophoresis band, and thus minimizing the gathering of the scattered radiation and background fluorescence from sources other than the band of interest. The subject apparatus in one embodiment can provide a dynamic range of about four orders of magnitude and can detect the fluorescence emission of about 1 ng of a common fluorescent agent, e.g. ethidium bromide.

The utility of the invention is not limited to the identification of molecular moieties; a set of colored dyes or inks forms a different but analogous multi-component system for document printing, for example. By scanning the document, the wavelength of light, the identity of the ink or dye, and the color of the document from each sample region may be determined.

The system may be viewed as comprising several primary components, and some optional components. The system has a light collection system for gathering and focusing a beam of light; means for selectively directing predetermined fractions of the received beam at each wavelength into two output beams; a detector for each of the two output beams to measure the intensity of each beam; and computation means including a special algorithm for determining the wavelength of the emitted radiation based on the two detector measurements and other predetermined system parameters. An excitation source to irradiate the sample so that it emits, reflects, or transmits some of the radiation is also required, but may be included within the device or provided externally.

The system uses inexpensive optical components that can be made in virtually any reasonable size, uses stable inexpensive solid state photodetectors that are interfaced to a computer with analog-to-digital converters, and uses an algorithm that can be implemented in inexpensive readily available microprocessor based computers.

While the means for separating the beam is a custom optical component, most of the other optical components needed for the system are generally commercially available and can be assembled with a very high degree of unit-to-unit uniformity. Because the components can be firmly mounted to rigid supports and no moving parts are used in the optical unit, the system is inherently stable and less susceptible to shock or vibration induced misalignment. The system further includes a self-calibration feature to compensate for possible variations, particularly the output aging characteristics of some lamps that may be used to irradiate the sample.

The system and method according to the present invention utilize the combination of a wavelength selective beamsplitter to separate radiation into two beams and an algorithm using predetermined system parameters and specially chosen functions of an intensity measurement of each beam (the ratio, difference, and geometric mean value) to perform sophisticated wavelength discrimination that previously required complex and expensive hardware in a conventional apparatus. The system and method of the present invention significantly simplify the design, improve the stability, and increase sensitivity by ignoring conventional design approaches and by eliminating many of the optical components conventionally included to improve performance. Systems using conventional narrow wavelength band transition dichroic beamsplitters are not capable of determining the wavelength of radiation over the broad wavelength range and with the accuracy of the present invention.

The system is particularly useful in scanning small areas, particularly narrow bands of about 1 to 10 $mm^2$, where there can be substantial background and it is desirable to minimize the light received from other than the sample.

The components of several embodiments of the system are now described. A simple embodiment is illustrated in FIG. 2. FIG. 2A is an illustration of the external beamsplitter housing 68. FIG. 2B is a sectional view through beamsplitter housing 68. FIG. 2C is a different sectional view through housing 68 which also illustrates the relationship between the optical and electronic components of the system. In this embodiment, a radiation source 30 powered by a power supply and control 31 is used to irradiate the sample 28, the choice of the radiation source depending upon the characteristics of sample 28, and the desired wavelength measurement, among other factors. An appropriate irradiation source is used to provide light in the wavelength range of interest, ultraviolet, visible, infrared, or a combination thereof. While a narrow band light source may be used, e.g. a laser, usually a broad band light source will be used, e.g. blacklight or a filtered mercury lamp. For fluorescence, the radiation source will provide light at least in the excitation band or bands of the fluorescers of interest and will usually be of a broad wavelength range, e.g. from about 250 nm to 1100 nm, and specifically from about 300 nm to about 800 nm. The source may be located so that the sample is irradiated to assure sufficient intensity and uniformity.

The radiation from the sample is gathered by the system into a beam and the beam directed towards a wavelength selective beamsplitter that provides for selectively directing predetermined fractions of the beam of emitted radiation at each wavelength respectively into each of first and second output beams over a predefined wavelength range. In one embodiment of the beam splitter, the predetermined fractions increase in the first output beam and decrease in the second output beam with increasing wavelength. Alternatively, the beam splitter may split the beam such that the predetermined fractions decrease in the first output beam and increase in the second output beam with increasing wavelength. The sum of the fractions in the first output beam and the sum of the fractions in the second output beam remains substantially constant at each wavelength within the predefined wavelength range. The beamsplitter is positioned to intercept radiation entering the system through an entrance aperture 32. Aperture 32 may take the form of a hole, slot, cylindrical tube, or other structure that restricts the angle from which radiation may enter, particularly shaped to minimize extraneous light entering the aperture. For an electrophoresis band, the aperture will usually be rectangular.

In one embodiment, the wavelength selective beamsplitter element is termed a Linear Wavelength Filter (LWF) 34. In the subject beamsplitter, the characteristic of the beamsplitter is to greatly expand the transition region, where the fraction of light reflected and the light transmitted varies substantially linearly in opposing directions with increasing wavelength. The transition region will generally extend over at least 50 nm usually at least about 300 nm, and may be over 400 nm or greater, usually at least about 300 nm.

The LWF is produced by alternating layers of high and low index of refraction materials of varying thicknesses and quarter wavelength optical thicknesses (Q.W.O.T.). The high and low index layers comprise substantially saturated oxides of titanium and silicon which are prepared by ion-assisted, reactive vacuum deposition of electron beam evaporated sub-oxides of the materials, A particular LWF which finds use has the following physical and optical properties:

TABLE 1

LINEAR WAVELENGTH FILTER
incident medium 1.0000

| LAYER | MAT'L | INDEX | THICKNESS |
|---|---|---|---|
| 1 | H | 2.411 | 91.8560 |
| 2 | L | 1.459 | 24.4937 |
| 3 | H | 2.411 | 65.0692 |
| 4 | L | 1.459 | 93.6640 |
| 5 | H | 2.411 | 47.5005 |
| 6 | L | 1.459 | 90.7248 |
| 7 | H | 2.411 | 24.6178 |
| 8 | L | 1.459 | 80.1435 |
| 9 | H | 2.411 | 48.2597 |
| 10 | L | 1.459 | 76.0285 |
| 11 | H | 2.411 | 18.5447 |
| 12 | L | 1.459 | 100.7182 |
| 13 | H | 2.411 | 45.8738 |
| 14 | L | 1.459 | 22.5342 |
| 15 | H | 2.411 | 55.7426 |
| 16 | L | 1.459 | 48.9875 |
| 17 | H | 2.411 | 13.6645 |

| MATERIAL | TOTAL PHYS THICK | TOTAL Q.W.O.T. |
|---|---|---|
| L | 537.2937 | 2741.9980 |
| H | 411.1284 | 3790.9978 |

Total physical thickness - 948.422 NANOMETERS (0.03734 MILS)
Substrate index - 1.520

The total thickness of the low index of refraction material will be about 535–540 nm, and the high index of refraction material will be about 410–412 nm.

Figure 3:
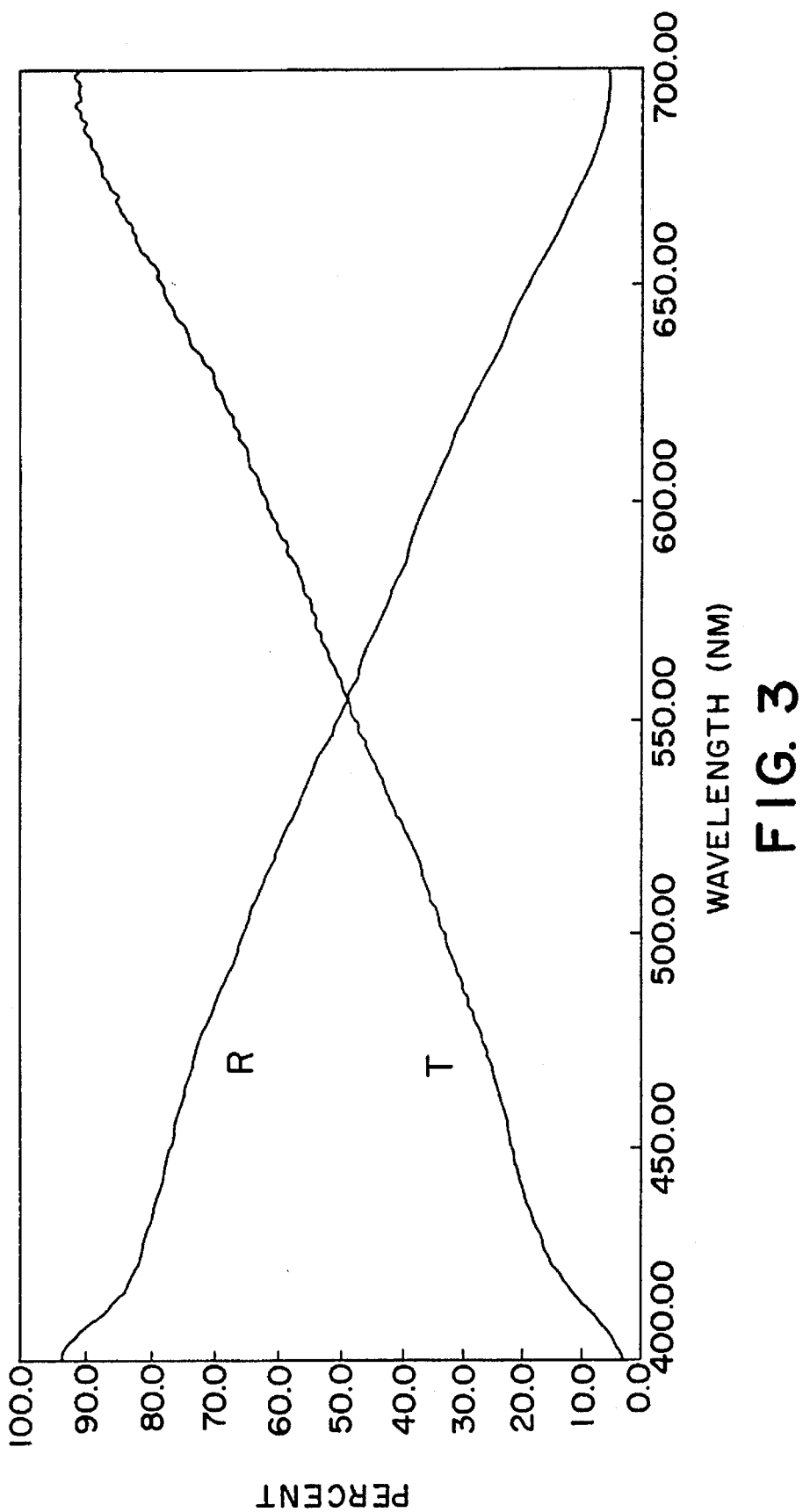
FIG. 3 is an illustration of a Linear Wavelength Filter transmission-reflection versus wavelength characteristic.

The transmission-reflection versus wavelength characteristic for a mildly idealized LWF 34 for an angle of incidence of 45 degrees is illustrated in FIG. 3. At about 400 nm the exemplary LWF 34 reflects between about 90% and 98% of incident light, more typically between about 92% and 94%. At about 700 nm the LWF reflects between about 0% and 10%, more typically between about 0% and 5%. Except for nominal amounts (less than about 10%), substantially little radiation is absorbed by the LWF over the predefined wavelength range. Substantially all radiation that is not reflected is transmitted, and vice versa.

FIG. 3 also illustrates the extended wavelength range over which the wavelength selective features of the LWF can be operative. The slope of the transfer characteristic of the Linear Wavelength Filter characteristic within its transition region (the predefined wavelength range) is gentle compared to the slope in the transition region of conventional filters.

Substantially strict linearity of the filter is not an essential requirement for operation of the system or method, monotonic performance, i.e. smoothly increasing or decreasing percent transmission as a function of wavelength, is preferred because it results in greater wavelength discrimination resolution and excludes ambiguities. A non-linear wavelength filter (NLWF) having substantially the same properties as the LWF but wherein the transmissivity and reflectivity change with wavelength in a non-linear manner may be used as long as the non-linearity is confined to a narrow wavelength range.

The LWF 34 comprises a substrate 36 on which dielectric layers are deposited to form dielectric cavities. A coating 38 comprising a plurality of layers, is deposited on substrate 36, typically a glass or crystalline material which is substantially optically clear over the wavelength range of interest. The correct thickness and composition of each layer are necessary to achieve the proper wavelength selective reflection/ transmission properties. (See for example, Handbook of Optics, W. G. Driscoll and W. Vaughan editors, McGraw-Hill Publishing Company, 1978, pp. 8-1 through 8–124, herein incorporated by reference, for a general discussion of filters and coatings.)

In one embodiment of the invention, a LWF 34 oriented at about a 45-degree angle to the center of incident beam 40 is used. Transmitted beam 42 continues along the direction of the incident beam 40, while reflected beam 44 is redirected at about 90 degrees to the original beam direction. The structure of the multi-layer dielectric coating 38 is optimized for the 45-degree geometry, but different coating structures may be fabricated for other geometries. A suitable Linear Wavelength Filter is provided by Optical Coating Laboratory Incorporated (OCLI), 2789 Northpoint Parkway, Santa Rosa, Calif., 95407-7397.

Each of transmitted beam 42 and reflected beam 44 are intercepted by separate radiation detectors 46 and 48, respectively, that provide means for measuring the amount of radiation in each of the two output beams. A single detector could be used by reflecting the transmitted light to the single detector, and using a chopper to alternate the beam which the detector receives. Each detector has an active area 50, 52 sufficiently large to intercept and collect the entire incident beam of radiation 42, 44. The radiation detector for each beam is desirably of the same type, but need not be. For maximum absolute system sensitivity and minimum expense it is desirable that there be no additional optics between the LWF 34 and detectors 46, 48. However, where the size of the beam exceeds the active area of detector 46, 48, beam reshaping optics (not shown) may optionally be interposed to match the beam sizes exiting LWF 34 to the active areas of the detectors. The detectors are sensitive to the wavelengths of interest. In the embodiment described above, the detectors should be sensitive over at least the wavelength range of interest, eg. of the LWF, from about 400 nm to about 750 nm.

A number of suitable detectors made from a variety of materials are known in the art and may be used. Solid-state silicon based (Si) detectors are convenient and generally available. The quantum efficiency of a typical silicon detector is not constant and typically ranges from about 0.2 at 400 nm, to about 0.8 at 850 nm, and then decreases to about zero at 1100 nm. The spectral responsivity or sensitivity characteristics of each detector 46, 48 are taken into account by the algorithms.

The sensitivity of silicon is biased toward greater sensitivity in the red and near-infrared. In one embodiment of the apparatus, the sensitivity from 400 nm to 800 nm has been partially equalized by interposing a ¼-wave anti-reflection coating in front of each detector. The anti-reflection coating is optimized to enhance the response in the blue region of the spectrum at the expense of some loss of response in the red region. However, while desirable to more nearly equalize the wavelength determination resolution over the predefined wavelength range, such an additional detector filtration is not necessary to practice the invention.

Other detector technologies may be used with the invention, such as a photo-multiplier tube. However, the size and complexity associated with integrating them into a system make their incorporation desirable only if the additional sensitivity is essential, and the larger size, greater expense, and increased complexity can be tolerated.

Each of the two radiation detectors 46, 48 provides a measurement of the amount of radiation (number of photons) striking each detector and generates an analog signal 54, 56 related to the amount of radiation in each of the beams. One detector receives a proportion of radiation that increases with increasing wavelength, while the other detector receives a proportion of radiation that decreases with increasing wavelength. Apparatus and methods for configuring detectors to generate appropriate analog signals 54, 56 (such as power supplies, amplifiers, and so forth) are known in the art and are not further described.

The LWF 34, and detectors 46, 48 are mounted in an optically opaque beamsplitter housing 68 that mounts the components in a stable manner and prevents stray light from sources other than sample 28 from striking LWF 34 or detectors 46, 48. Such a housing 68 may be made from any suitable material, including metal, plastic, and so on, with consideration given to minimizing the thermal expansion of the material under the conditions of use.

The analog signals 54, 56 are communicated to analog-to-digital converters (A/D) 58, 60 to convert analog signals 54, 56 into digital signals or values 62, 64 suitable for use with computer 66, such as a microprocessor based digital computer. The communication is generally accomplished with electrical wires, preferably with shielding to reduce noise. A/D converters may also be integrated into the detector electronics or be contained within computer 66.

Computer 66 computes the wavelength of the emitted radiation 40 using an algorithm 70 including an appropriate Fourier analysis of the different characteristics in the light detected by photodetectors 46, 48 and selected predetermined system parameters, including the characteristics of LWF 34 and the responsivity characteristic of each detector 46, 48. The Fourier analysis provides means for determining the wavelength, including the center wavelength and some error bounds, of the emitted beam from the two measured amounts of radiation and the predetermined system characteristics. The ratio, geometric mean value, and difference of the two measured amounts are used in the determination.

The Fourier analysis is a wavelength dispersive analysis performed by overlaying the transformed polynomial derived according to the transmission-reflection characteristic profiles of the LWF and the detector spectral sensitivity characteristics, and including any detector equalization filters that may be present to provide a unique wavelength solution. A chromatic resolution of at least about 25 nm can be achieved, using this system and method. See Ruckdeschel, F. R., Basic Scientific Subroutines (1981) Vol. 1–Vol. 2.

In the general case, the wavelength discrimination resolution determined by Fourier analysis is related to the mathematical order of the filter characteristic. The lower the order the better the wavelength discrimination; a first order system providing the best discrimination. The LWF has a first-order linear characteristic and is therefore capable of producing the most accurate discrimination. By comparison, most absorption type filters have a higher order non-linear filter characteristic and provide a poorer discrimination.

The Fourier analysis is most easily carried out using computer 66 such as a microprocessor based digital computer. Any of numerous types known in the art may be used, or their equivalent incorporated into a single instrument containing the optics and electronics. Such computers may commonly incorporate keyboard and display for interacting with the computer, storage devices, internal memory, and assorted standard peripherals.

Figure 4:
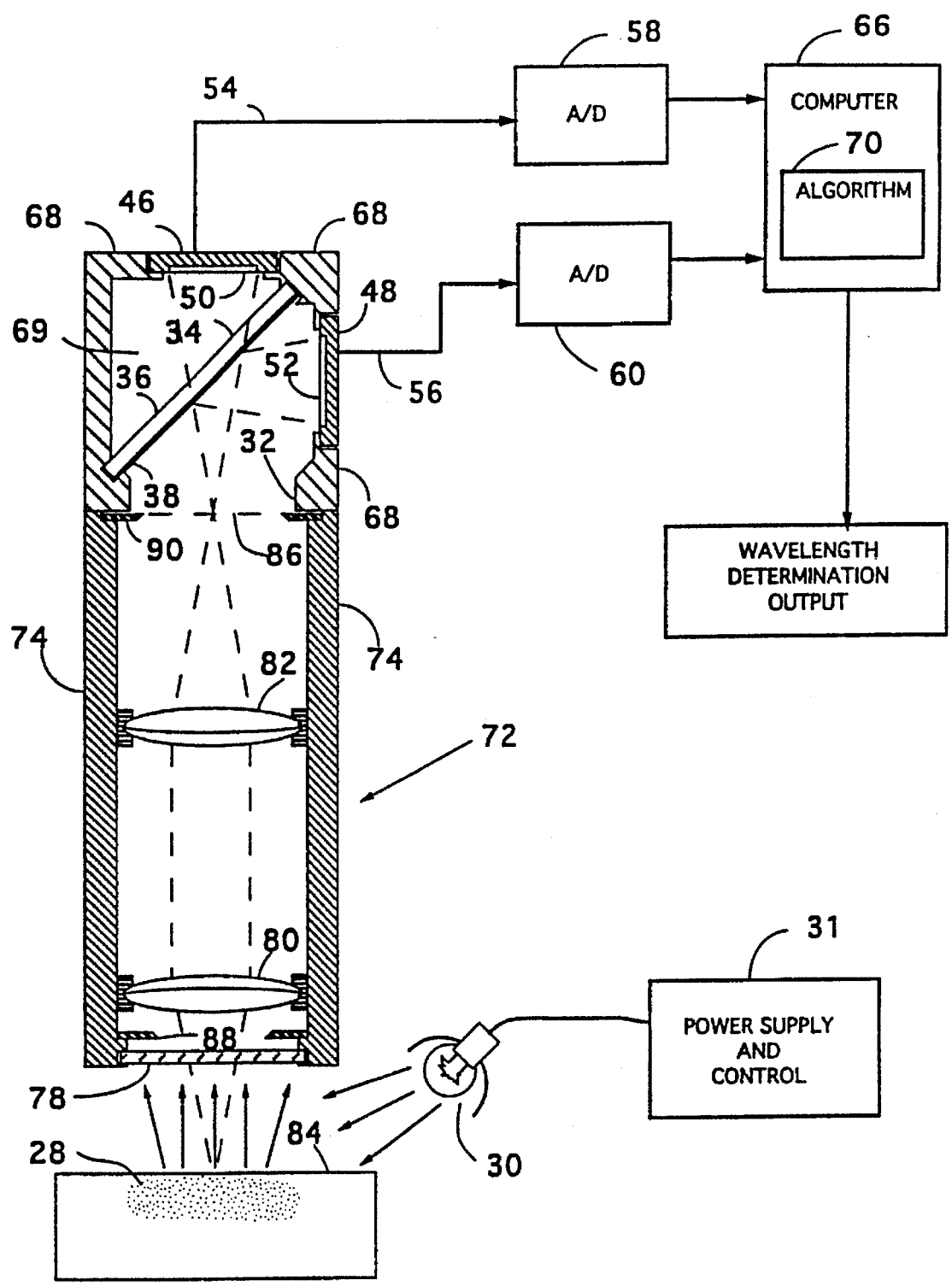
FIG. 4 is an illustration of another embodiment of a system incorporating additional collection optics.

A more sophisticated embodiment is illustrated in FIG. 4. Elements with like reference numerals have like characteristics. This embodiment, comprises the same elements as in the simple embodiment but further comprises an additional light collection unit 72 that is optically interfaced to the wavelength separation and detection components described in the simple embodiment above. The external and internal characteristics of beamsplitter housing 68 as illustrated in FIG. 2A–C are the same as in the embodiment shown in FIG. 4 and are not shown. The light collection unit 72 is generally interposed between aperture 32 and sample 28 of the simple embodiment. The location and/or spatial beam characteristics of source 30 may be somewhat optimized to generally match the sample region to be measured, when the region is spatially limited by light collection unit 72, as described below.

Light collection unit 72 comprises an optical housing 74 having a hollow cylindrical bore within its interior. Optical housing 74 may be combined with beamsplitter housing 68 to provide a single unit. The external shape of the housing and internal bore are not particularly important. Any external housing shape or internal cavity bore shape that facilitates mounting of the optical components, and that does not interfere with other portions of the system, or block portions of the various beams is acceptable. Having a cylindrical internal cavity bore is preferred. Housing 72 should be optically opaque to the radiations of the wavelengths of interest, or to which detectors 46, 48 are sensitive.

In one embodiment of the invention, the optical housing 74 is rectangular and made of aluminum that is approximately 4.5 cm long. It has an internal diameter of about 12 mm. The optical components are mounted by sleeves and fixed with set screws extending through the housing.

A band-pass filter 78 is provided in the optical configuration where radiation from the sample enters light collection unit 72. The optical transmission characteristics of band-pass filter 78 are selected to transmit only the wavelengths from sample 28 that are to be measured by detectors 46, 48. In the case of fluorescent labels, band-pass filter 78 should desirably be transmissive only to the wavelength range of interest.

Band-pass filter 78 may provide particular advantages when ultraviolet light is used to excite florescent markers in a sample. Many standard optical components, including many optical glasses, fluoresce in the visible wavelengths when irradiated by ultraviolet light. Any such optical component fluorescence will appear as a false signal component that may interfere with the desired measurement. Band-pass filter 78 prevents scattered and reflected angled light from entering the collection system.

The band-pass filter 78 may be changed to pass and block the appropriate wavelengths, depending on the wavelength range of interest. For example, filter 78 may be changed when investigating different components where fluorescent labels having different emission wavelengths are used for each component. For example, when ethidium bromide is used as the sole fluorescent marker, a band-pass filter that passes wavelengths in some bandwidth around 610 nm may be used.

Re-imaging optics 80, 82 are provided for re-imaging sample focal plane 84 within sample 28, to a re-image plane 86. Any suitable optical configuration that provides sufficient light collection capability for the required sensitivity, and that has a sufficiently large numerical aperture to provide the required spatial resolution at the sample, can in principle be used to re-image. However, an additional consideration and possible restriction applies to multi-channel systems where the optical re-imaging system must be substantially the same for each channel. Such similarity provides the uniformity between channels desirable for inter-channel comparisons.

In principal, spherical or aspherical components, formed by either grinding or molding glass or plastic can be used. In certain configurations, cylindrical optical components may be used but have been found to be sub-optimal because of cross-talk in multiple-channel configurations.

In one embodiment of the system, each of the re-imaging optics 80, 82 comprise a pair of first and second cemented doublet achromats 80, 82 configured in a 1:1 conjugate ratio. Each achromat has a diameter of about 12.5 mm, a focal length of about 25 mm, and a half angle of view of about 5 degrees. Using this optical configuration, this embodiment was designed to achieve a spatial resolution such that the ±2 sigma point on the point spread function was less than about 200 micrometers. The design of optical systems to achieve desired light collection and resolution goals is known in the art and need not described further. Where the sample has a thickness greater than the depth of focus of the re-imaging optical system and is at least somewhat transparent, such as a gel or liquid, the focal plane 84 location within the sample 28 may be adjusted to image the desired region. Optical components such as re-imaging lenses 80, 82 are made from materials that are optically clear over the wavelength range of interest, and include optical glasses and crystalline materials.

Achromatic lenses primarily correct for color aberration. Field curvature and spherical aberration are still generally present. These aberrations degrade the entire image and are most severe for off-axis image points. The effects of the aberrations are minimized by limiting the off-axis imaging to the actual sample region to be measured rather than accepting all the radiation within the optical field of view. For applications that measure the properties of a rectangular sample region, such as a long narrow slit shaped region used in a gel electrophoresis application (described below), it is advantageous to provide a similarly shaped aperture 88 between sample 28 and re-imaging optics 80, 82 to reduce the angle of acceptance to the minimum required. This reduces the effect of spherical aberration and field curvature. Radiation from outside the narrow rectangle measurement region of sample 28 does not enter the re-imaging optical system and therefore does not contribute energy to the aberration components of the image which would otherwise be present throughout re-image plane 86. Using the achromats at a 1:1 conjugate ratio also reduces overall aberrations because some aberrations from each of lenses 80, 82 may tend to cancel as in known in the art.

Aspheric optics correct for spherical aberration and would generally be well suited for the re-imaging optics except for two potential problems. First, they are more expensive and more difficult to make. Second, it is more difficult to manufacture multiple aspheric lenses that are substantially the same, especially if molded, rather than ground, aspheric optics are used.

The re-imaging optics 80, 82 are desirably anti-reflection coated to maximize transmission. Single or multi-layer coatings may be used.

A second aperture 90 is located at the focal plane of second achromat 82. This focal plane is also substantially coincident with re-image plane 86. Aperture 90 has a similar shape and may have substantially the same shape as the sample region to be measured. When 1:1 re-imaging conjugates are used, the size of aperture 90 is also substantially the same as the sample region to be measured. If other than 1:1 conjugates are used so that there is an effective magnification, then the size of aperture 90 should be scaled accordingly so that its size substantially matches the image of sample region 28 in the re-image plane 86. This second aperture 90 blocks emitted radiation arriving from areas of the sample outside of a predetermined measurement region of the sample. Apertures 88, 90 can be made of beryllium copper, aluminum, stainless steel, or can be made of any other suitable optically-opaque material. The shape and dimensions of apertures 88, 90 can be chosen to define the sample region to be measured and angle of acceptance.

In an embodiment of the present invention used in conjunction with a gel electrophoresis system, aperture 90 is a long narrow slit about 100 μm×about 10 mm. Either or both the gel media, and the subject device are moved incrementally in a substantially linear fashion relative to each other so that areas of the gel may be sequentially measured at about 200 μm spatial intervals. At each incremental location a measurement of the intensity in each beam based on the radiation emitted from the sample in the 200 μm×10 mm area is made according to the present invention. These measurements permit a determination of the presence and wavelength of fluorescent light at each location so that the migration of the bands in the gel electrophoresis can be monitored.

Figure 5:
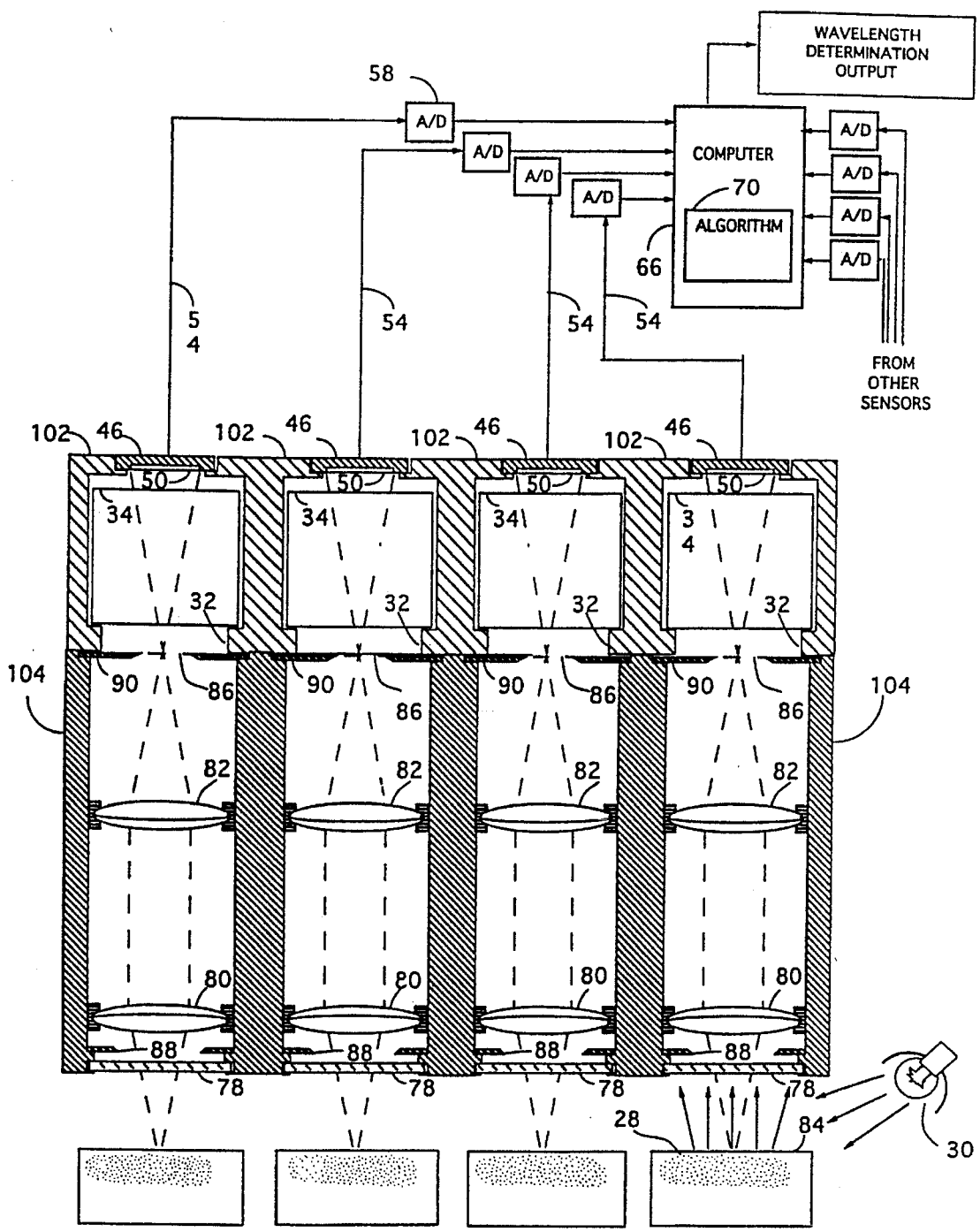
FIG. 5 is an illustration of a multiple-channel embodiment of a system according to the present invention.

A multiple-channel embodiment of the invention is illustrated in FIG. 5. Four channels are illustrated, but configurations comprising any number of channels, such as 8, 15, 32, or more channels may be used. Each channel comprises light collection optics, beam separation, and beam detection components as previously described. However, an instrument incorporating multiple channels may share radiation sources 30 and power supply and control 31, particularly as a single elongated source, and may be interfaced to a single computer 66. Only a single radiation source 30 is shown. Separate analog-to-digital converters 58, 60 may be used for each channel, or a pair of A/D converters may be multiplexed between channels. Such techniques are known in the art and not discussed further.

In the embodiment illustrated in FIG. 5, a two piece multi-channel housing 102, 104 is provided. Beam separator and detector housing 102 contains LWF 34, and the plurality of pairs of detectors 46, 48 (not shown). Aperture 90 is located within housing 104 in this embodiment, but may alternatively be mounted to light collection unit housing 102.

LWF 34, aperture 88, and/or aperture 90 may be fabricated and mounted as separate discrete components in each channel, or may be fabricated as a single strip or array. For example, apertures 88, 90 may be fabricated as an array of spaced apertures along a single strip of material. A single piece LWF has the problem of cross-talk that may occur between channels as a result of light-piping within the LWF coating or substrate, but may be easier to fabricate and does not require individual alignment. Preferably, the LWF is fabricated in a single piece to facilitate uniformity between channels, and then cut and mounted as discrete components in each channel, as illustrated in FIG. 5.

Figure 6:
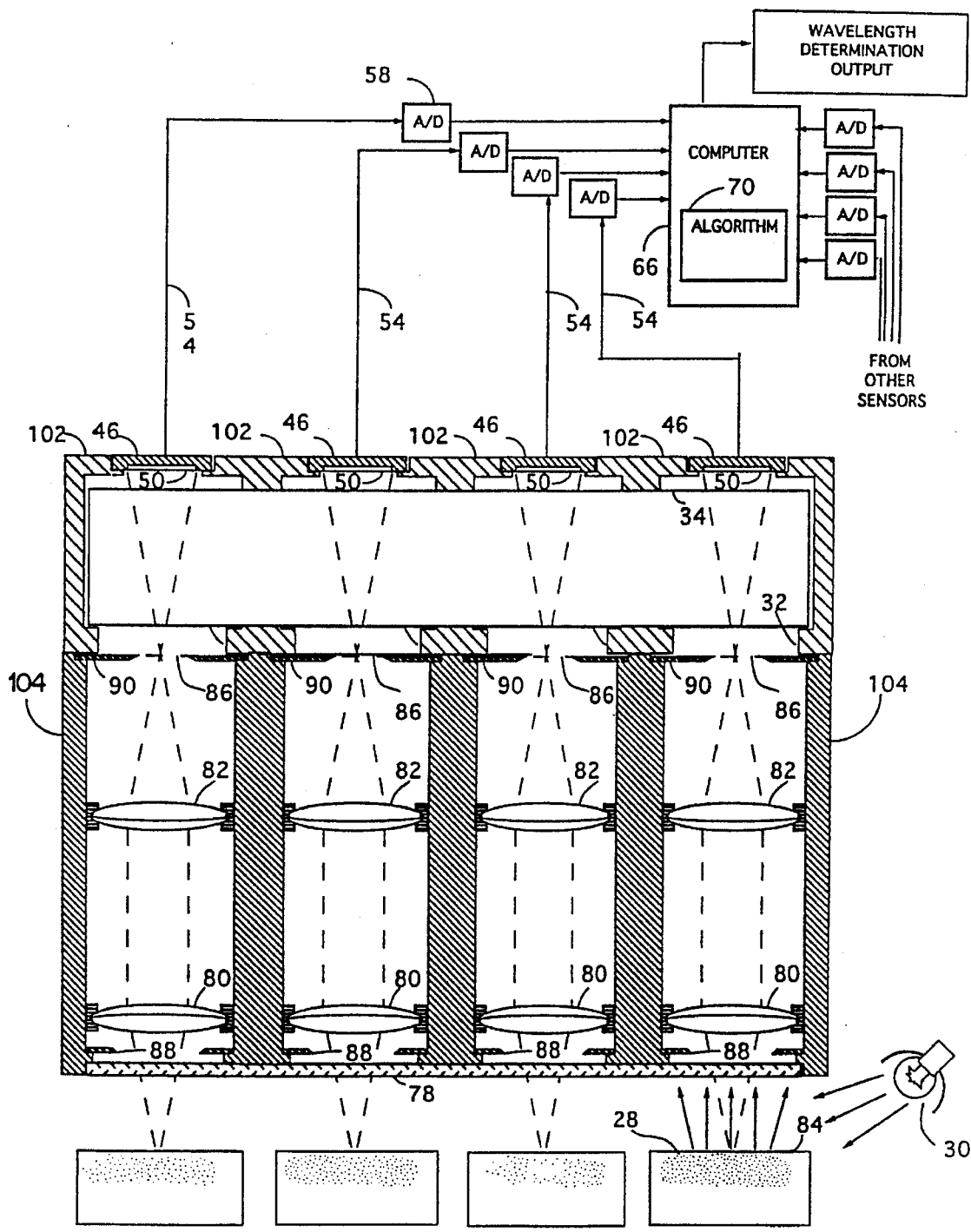
FIG. 6 is an illustration of a second multiple-channel embodiment of a system according to the present invention.

Alternatively, though not preferred, LWF 34 may be fabricated on a single substrate 36 and mounted in a slot 106 spanning the optical paths of multiple channels, as illustrated in the embodiment in FIG. 6. The embodiment of FIG. 6 also incorporates a single piece band-pass filter 78 spanning the several channels.

The various components are mounted in housings 102, 104 using conventional techniques that are known in the mechanical and optical arts.

Of particular interest is mounting of the system on a movable platform, where the art systems moved in a controlled manner, e.g. stepwise, so as dynamically scan a surface. The steps can be chosen to be up to one half of each area scanned or may overlap or may leave areas unscanned, depending on the needs of the system being analyzed. By using a stepping motor, the position of the system can be located. Other means may be used to locate the position of the system, so that the information may be forwarded to the computer to define where the band is in real time during a gel electrophoresis run. In this manner, the gel may be repetitively scanned and the movement of the bands monitored, so that the run may be stopped when the desired separation has been achieved.

The multi-channel configuration is not restricted to a linear array of channels, and other geometrical configurations, such as circles, arcs, and so on are clearly within the scope of the invention.

Having described the various components of the system, the use of the system and its various applications will now be considered.

A multi-channel embodiment according to the present invention is particularly suitable for determining the spectral characteristics of samples in a gel electrophoresis system. For example, U.S. Pat. No. 5,104,512, the contents of which are herein incorporated by reference, discloses a gel electrophoresis system. Embodiments of that system comprise a spectrophotometer means for monitoring the movement of fractions in the gel. A multiple channel embodiment of the present invention can be substituted for that spectrophotometer and provide improved spatial resolution because of the larger numerical aperture, and greater sensitivity because of its greater light gathering capability.

The detectors of the subject device may be mounted on the head of a catheter and introduced into the vascular system to observe fluorescent tagged sites.

It is evident from the foregoing description that the present invention has several advantages over the prior art. It provides the potential of a very compact low cost system having no moving parts in the optical system. The optical system has low power consumption and generates little if any heat and therefore can be sealed. The system is efficient because light is not wasted by the use of absorption type filters or by pre-splitting the emitted beam into multiple channels for subsequent filtration. The spectral wavelength resolution is not a function of signal strength; although at very small signal levels, the error in the wavelength determination does increase. The determination involves only one measurement from each of two signal channels, thereby simplifying computer hardware and software algorithm requirements. Its lack of electro-mechanical components and the simplicity of the system allow very rapid measurement so that the system can be used in a rapid scanning mode. It is efficient since all the incident light is split between two detectors with only minor surface losses in the detectors and the LWF. The efficiencies permit the use of less costly solid-state photodetectors in lieu of photo-multiplier tubes.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A system for determining the wavelength of radiation coming from a sample, said system comprising:

means for forming a beam of radiation from radiation coming from a small area;

linear wavelength filter means for selectively directing predetermined fractions of said beam of radiation at each wavelength within a wavelength range of at least about 300 nm by either reflectance or transmission into two output beams over a predefined wavelength range, said predetermined fractions increasing in one of said output beams and decreasing in the other of said output beams with increasing wavelength, wherein the radiation loss from said selectively directing means is small and relatively insensitive to wavelength;

means for measuring the total amount of radiation in each of said output beams; and means for determining the wavelength of said emitted beam from said two measured amounts of radiation.

2. The system as in claim 1, wherein said predefined wavelength range is greater than about 300 nm and is in the range of about 300 to 750 nm.

3. The system as in claim 1, wherein said means for determining comprises means for performing a Fourier wavelength dispersive analysis of said measured amounts of radiation.

4. The system as in claim 3, wherein said means for determining further includes values for the spectral wavelength characteristics of said linear wavelength filter means and of said means for measuring.

5. The system as in claim 1, wherein said increasing and said decreasing of said predetermined fractions by reflectance or transmission with increasing wavelength is substantially linear.

6. A system for determining the wavelength of radiation emitted from a predetermined spatial region of a sample, said system comprising:

means for irradiating a sample region to produce emitted radiation;

an optically opaque housing positioned for receiving said emitted radiation;

band-pass filter means for transmitting a predefined wavelength range of interest;

optical means for optically re-imaging a region of said sample to a predetermined re-imaging plane;

first aperture means for limiting the angle of acceptance of said optical means for re-imaging;

second aperture means for collecting portions of said emitted radiation by blocking any of said emitted radiation arriving from areas outside of a predetermined spatial region of said sample;

linear wavelength filter means for selectively directing predetermined fractions of said beam of radiation at each wavelength within a wavelength range of at least about 300 nm by either reflectance or transmission into two output beams over a predefined wavelength range, said predetermined fractions increasing in one of said output beams and decreasing in the other of said output beams with increasing wavelength, wherein the radiation loss from said selectively directing means is small and relatively insensitive to wavelength;

means for measuring the total amount of radiation in each of said output beams; and means for determining the wavelength of said emitted beam from said two measured amounts of radiation:

said band-pass filter means, said first aperture means, said optical means for re-imaging, said second aperture means, and said means for selectively directing predetermined fractions, being aligned along a common optical path and located within said optically opaque housing.

7. A system for determining the wavelengths of radiations emitted from each of a plurality of sample regions, said system comprising:

means for irradiating each of said plurality of sample regions to produce emitted radiation from each said sample region;

an optically opaque multiple channel housing for receiving said emitted radiation from a plurality of small areas;

a plurality of separate analysis channels, each said channel configured for evaluating radiation emitted from a different sample region, each said channel being substantially optically isolated from each said other channel;

each said analysis channel comprising:

band-pass filter means for transmitting a predefined wavelength range of interest;

optical means for optically re-imaging a region of said sample to a predetermined re-imaging plane;

first aperture means for limiting the angle of acceptance of said optical means for re-imaging;

second aperture means for collecting portions of said emitted radiation by blocking any of said emitted radiation arriving from areas outside of a predetermined spatial region of said sample;

means for selectively directing predetermined fractions of said collected portion of said emitted radiation at each wavelength respectively into two output beams over a predefined wavelength range of at least 300 nm, said predetermined fractions increasing in one of said output beams and decreasing in the other of said output beams with increasing wavelength, wherein the radiation loss from said selectively directing means is small and relatively insensitive to wavelength;

means for measuring an amount of radiation in each of said output beams; and means for determining the wavelength of said collected portion of said beam of emitted radiation from said two measured amounts of radiation;

said band-pass filter means, said first aperture means, said optical means for re-imaging, said second aperture means, and said means for directing, being aligned along a common optical path and located within said optically opaque housing.

8. The system as in claim 7, wherein said predefined wavelength range is from about 400 nm to about 750 nm.

9. The system as in claim 7, wherein said means for selectively directing is a single piece Linear Wavelength Filter, and wherein said single piece Linear Wavelength Filter physically extends across said plurality of analysis channels.

10. The system as in claim 7, wherein said means for selectively directing is a Linear Wavelength Filter, and wherein each said channel comprises a physically distinct Linear Wavelength Filter.

11. A linear wavelength filter, substantially as defined in the following tabulation;

| LAYER | MAT'L | INDEX | THICKNESS |
|---|---|---|---|
| 1 | H | 2.411 | 91.8560 |
| 2 | L | 1.459 | 24.4937 |
| 3 | H | 2.411 | 65.0692 |
| 4 | L | 1.459 | 93.6640 |
| 5 | H | 2.411 | 47.5005 |
| 6 | L | 1.459 | 90.7248 |
| 7 | H | 2.411 | 24.6178 |
| 8 | L | 1.459 | 80.1435 |
| 9 | H | 2.411 | 48.2597 |
| 10 | L | 1.459 | 76.0285 |
| 11 | H | 2.411 | 18.5447 |
| 12 | L | 1.459 | 100.7182 |
| 13 | H | 2.411 | 45.8738 |
| 14 | L | 1.459 | 22.5342 |
| 15 | H | 2.411 | 55.7426 |
| 16 | L | 1.459 | 48.9875 |
| 17 | H | 2.411 | 13.6645 | wherein the incident medium is 1.0000;

| MATERIAL | TOTAL PHYS THICK | TOTAL Q.W.O.T. |
|---|---|---|
| L | 537.2937 | 2741.9980 |
| H | 411.1284 | 3790.9978 |

Total Physical thickness - 948.422 NANOMETERS (0.03734 MILS)
Substrate index - 1.520.

12. A method of determining the wavelength of a beam of emitted radiation from a small area, comprising the steps of:

forming a beam of radiation from radiation coming from said small area;

selectively directing predetermined fractions of said beam of radiation at each wavelength into two output beams over a predefined wavelength range of at least 300 nm, said predetermined fractions increasing in one of said output beams and decreasing in the other of said output beams with increasing wavelength, wherein the radiation loss from said selectively directing means is small and relatively insensitive to wavelength, measuring the total amount of radiation in each of said first and second output beams; and determining the wavelength of said emitted beam from said two measured amounts of radiation.

13. A method according to claim 12, said method further comprising repeating said method at a plurality of small areas.

14. A method for scanning a gel in a gel electrophoresis to detect fluorescent bands, said method comprising:

in a first series of determinations:

forming a plurality of beams of radiation from radiation coming from a plurality of small areas in a line orthogonal to the direction of movement of ions in said gel;

selectively directing predetermined fractions of each of said beams of radiation at each wavelength into two output beams over a predefined wavelength range of at least 300 nm, said predetermined fractions increasing in one of said output beams and decreasing in the other of said output beams with increasing wavelength, wherein the radiation loss from said selectively directing means is small and relatively insensitive to wavelength, measuring the total amount of radiation in each of said first and second output beams from each of said small areas;

determining the wavelength of each of said emitted beams from said two measured amounts of radiation for each of said small areas; and repeating said first series of determinations from a plurality of small areas adjacent to said plurality of small areas measured in said first series, until substantially all of said gel has been scanned.

* * * * *